US007856896B2

(12) United States Patent
Matsumoto (10) Patent No.: US 7,856,896 B2
(45) Date of Patent: Dec. 28, 2010

(54) ANALYZER (75) Inventor: Daisuke Matsumoto, Kyoto (JP)

(73) Assignee: Arkray, Inc., Kyoto (JP)

( * ) Notice: Subject to any disclaimer, the term of this patent is extended or adjusted under 35 U.S.C. 154(b) by 458 days.

(21) Appl. No.: 11/989,649

(22) PCT Filed: Jul. 27, 2006

(86) PCT No.: PCT/JP2006/314905

§ 371 (c)(1),
(2), (4) Date: Jan. 29, 2008

(87) PCT Pub. No.: WO2007/013562

PCT Pub. Date: Feb. 1, 2007

(65) Prior Publication Data

US 2009/0031829 A1   Feb. 5, 2009

(30) Foreign Application Priority Data

Jul. 29, 2005    (JP) .............................. 2005-222286

(51) Int. Cl.
G01N 1/38     (2006.01)
G01N 21/01    (2006.01)
G01N 21/29    (2006.01)
(52) U.S. Cl. .............. 73/863.33; 73/863.21; 73/863.61; 73/864.81; 422/57; 422/68.1; 422/103
(58) Field of Classification Search .............. 73/863.21, 73/64.56, 863.31, 863.33, 863.61, 864.81; 422/57–58, 68.1–69, 82.05, 99–100, 102–103
See application file for complete search history.

(56) References Cited

U.S. PATENT DOCUMENTS

| 5,469,751 | A | * | 11/1995 | Weiss et al. ............... 73/863.33 |
| 6,241,950 | B1 | * | 6/2001 | Veelenturf et al. .......... 422/103 |
| 6,717,136 | B2 | | 4/2004 | Anderson et al. |
| 6,919,058 | B2 | | 7/2005 | Andersson et al. |
| 7,047,795 | B2 | * | 5/2006 | Sato .......................... 73/64.56 |
| 2005/0087479 | A1 | | 4/2005 | Okada et al. |
| 2005/0282290 | A1 | * | 12/2005 | Fujimoto et al. ............ 436/180 |
| 2006/0008381 | A1 | | 1/2006 | Taguchi et al. |
| 2006/0045799 | A1 | | 3/2006 | Taguchi et al. |

FOREIGN PATENT DOCUMENTS

| JP | 9-138233 | 5/1997 |
| JP | 2003-215133 | 7/2003 |
| JP | 2004-117178 | 4/2004 |
| JP | 2004-150804 | 5/2004 |
| JP | 2005-502031 A | 1/2005 |

* cited by examiner

*Primary Examiner*—Thomas P Noland
(74) *Attorney, Agent, or Firm*—Hamre, Schumann, Mueller & Larson, P.C.

(57) ABSTRACT

The present invention relates to an analytical tool including a plurality of flow paths 21 each including a detection cell 26 for detecting a particular component contained in a sample and configured to move the sample by capillarity, and a common path 22 connecting the plurality of flow paths 21 to each other. Each of the flow paths 21 includes a water stopper 29 for preventing the sample from flowing into the common path 22. Preferably, the water stopper 29 suppresses the movement of the sample by differentiating a cross sectional area at a target portion in a direction perpendicular to the sample flow direction from a cross sectional area at a portion near the target portion.

19 Claims, 8 Drawing Sheets

ANALYZER

TECHNICAL FIELD

The present invention relates to an analytical tool including a plurality of flow paths though which a sample is moved by capillarity, where the flow paths are connected to each other via a common path.

BACKGROUND ART

In a conventional sample analyzing method, a reaction liquid is prepared by reacting a sample with a reagent, and then the reaction liquid is subjected to optical analyzation. To analyze a sample by this method, use may be made of an analytical tool for providing a reaction field. Such an analytical tool may be set into an analyzer configured to analyze the reaction liquid. When a small amount of sample is to be analyzed, a microdevice, formed with minute flow paths, is used as an analytical tool.

Figure 7:
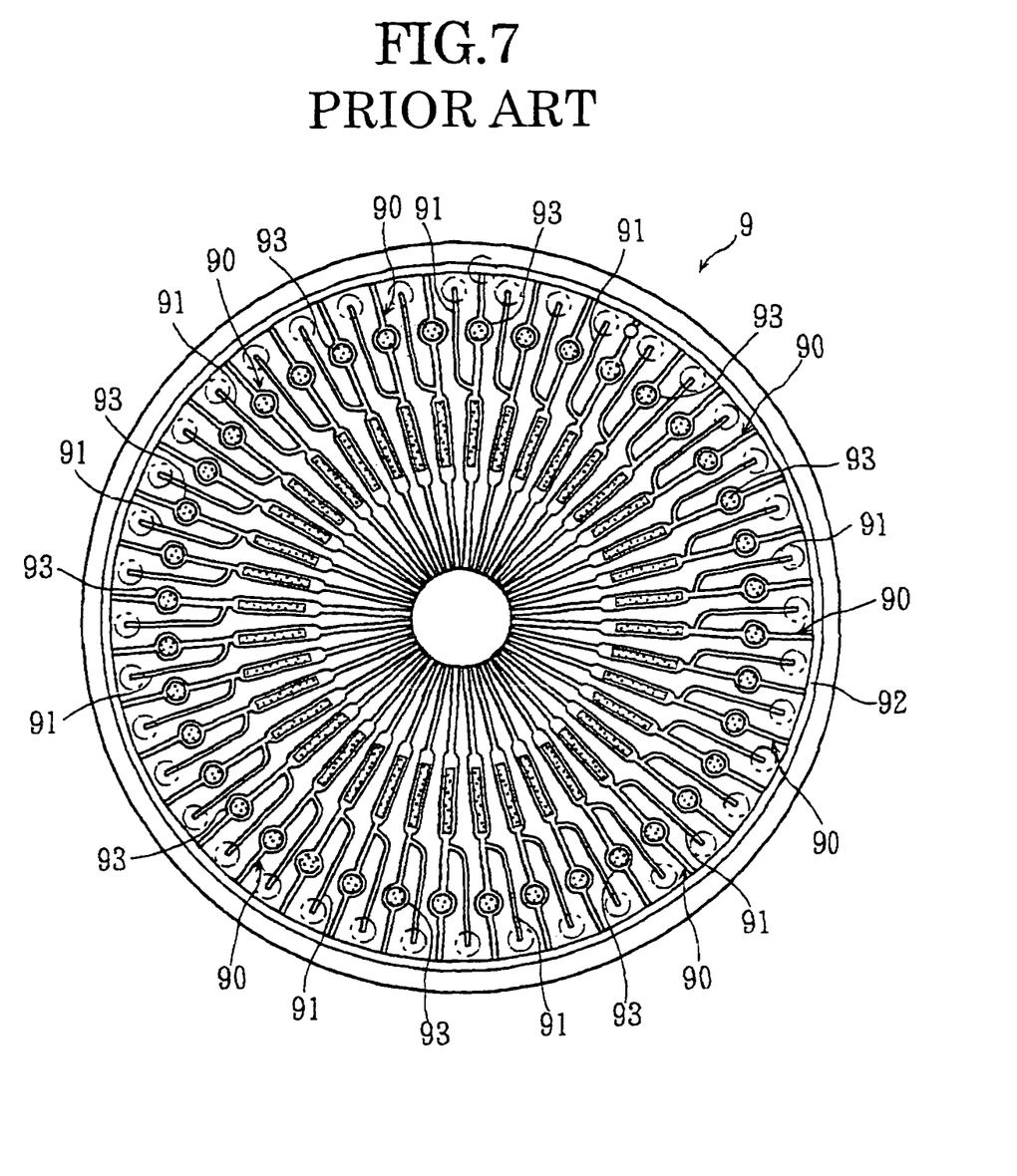
FIG. 7 is a plan view showing a substrate of a conventional microdevice.
Figure 8A:
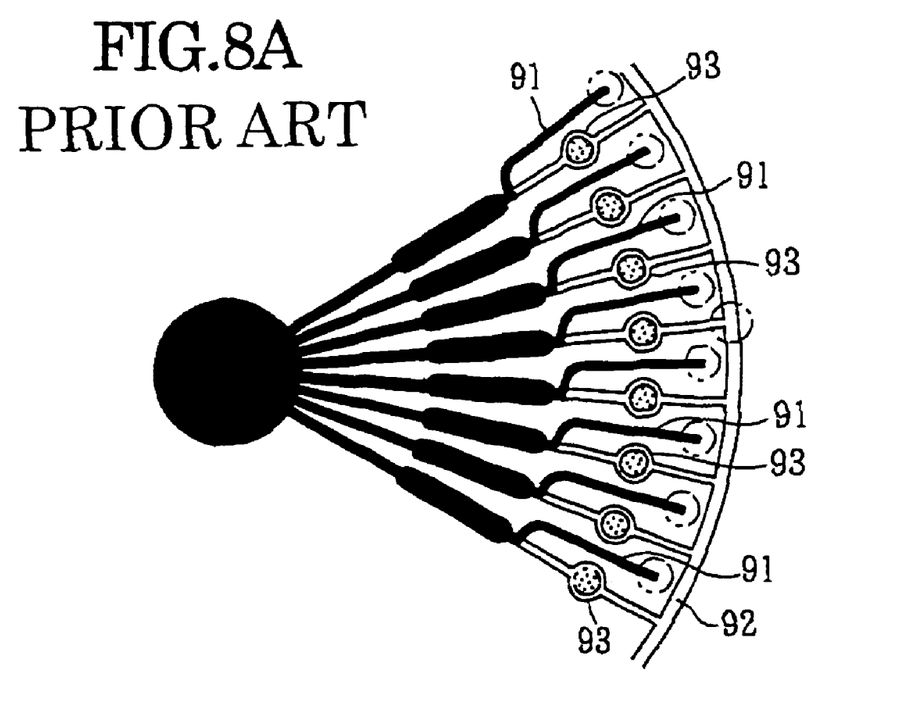
FIG. 8 is a schematic view for describing the operation of the microdevice shown in FIG. 7.
Figure 8B:
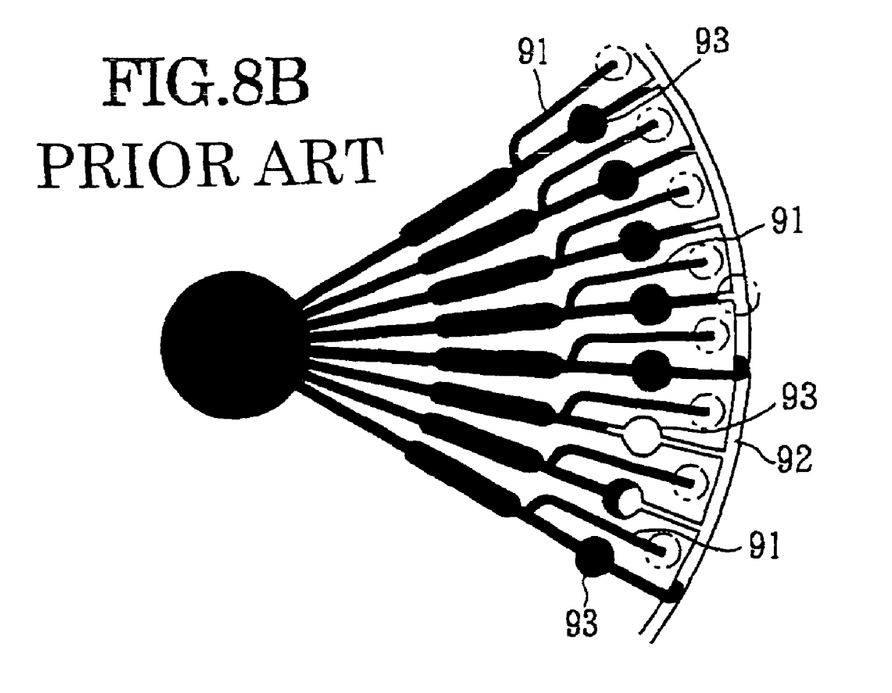

Referring now to FIG. 7, the conventional microdevice 9 includes a plurality of radially arranged flow paths 90 for moving a sample by capillarity (see Patent Document 1, for example). In the microdevice 9, a branch flow path 91 branches off from an intermediate portion of each flow path 90, and the end (downstream end in the sample flow direction) of each flow path 90 is connected to an annular common path 92. The branch flow paths 91 are configured to communicate with the outside. When communication is provided between the inside and the outside of the branch flow paths 91, the sample will flow into the branch flow paths 91, as shown in FIG. 8A. In each of the flow paths 90, the sample moves to the portion (branch portion) before a reaction portion 93 (provided with a reagent portion). The common path 92 is also arranged to communicate with the outside. Thus, in discharging gas from the common path, the sample is collectively introduced into the reaction portions 93 of the flow paths 90, as shown in FIG. 8B, and reacts with the reagent in the reagent portions 93.

However, the flow paths 90 of the microdevice 9 may have variations in e.g. volume (cross sectional area) due to an error in the manufacturing process, whereby the sample may flow at different speeds in the flow paths 90. If the sample moves at a higher speed through a certain flow path, thereby reaching the common path 92 earlier, only the particular portion of the sample may fill the path 92. In such a case, the capillary force becomes weaker in the other flow paths having lower sample moving speeds. In these flow paths, the movement of the sample may stop before a sufficient amount of sample has been supplied to the reaction portion 93, or the speed of the sample flowing into the reaction portion 93 may be considerably reduced. In these cases, the measurement accuracy for the slow-sample flow paths may deteriorate. In particular, the flow paths 90 of the microdevice 9 are very small. Consequently, the size variation due to the manufacturing error can significantly affect the speed of sample movement, thereby making the above problem more serious.

Patent Document 1: JP-A-2004-117178

DISCLOSURE OF THE INVENTION

Problems to be Solved by the Invention

An object of the present invention is to provide an analytical tool in which a plurality of flow paths for moving a sample by capillarity are connected to each other via a common path and which is capable of preventing the sample from flowing into the common path and thereby enhancing the measurement accuracy.

Means for Solving the Problems

According to the present invention, there is provided an analytical tool comprising a plurality of flow paths each including a detection cell for detecting a particular component contained in a sample and configured to move the sample by capillarity, and also comprising a common path connecting the plurality of flow paths to each other. Each of the flow paths includes a water stopper for preventing the sample from flowing into the common path.

For instance, the water stopper suppresses the movement of the sample by differentiating the cross sectional area at a target portion in a direction perpendicular to the sample flow direction from the cross sectional area at a portion near the target portion.

The water stopper may include at least one recess. In this case, a stepped portion is provided between the recess and a portion near the target portion.

The water stopper may be provided by a water-absorbent material or by performing water-repellent treatment with respect to a target portion.

Preferably, the water-absorbent material is arranged in the recess. As the water-absorbent material, use may be made of porous water-absorbent material, water-swellable polymeric material or water-curable polymeric material.

Preferably, the water-repellent treatment is performed with respect to the inner surface of the recess.

Each of the flow paths may include a main flow path in which the detection cell is provided and a branch flow path branching from the main flow path on an upstream side of the detection cell in the sample flow direction.

In the analytical tool according to the present invention, the main-flow path may not communicate with the common path, whereas the branch flow path may communicate with the common path. Preferably, in this case, the water stopper is provided in the branch flow path.

In the analytical tool according to the present invention, the main flow path may communicate with the common path, whereas the branch flow path may not communicate with the common path. Preferably, in this case, the water stopper is provided in the main flow path at a position downstream from the detection cell.

The flow paths may be radially arranged. In this case, the main flow path or the branch flow path includes a main flow path exhaust port for discharging gas from the detection cell or a branch flow path exhaust port for discharging gas from the branch flow path, and the common path includes a common path exhaust port for discharging gas from the common path. The common path exhaust port and the main flow path exhaust port or the branch flow path exhaust port are arranged on a common circle. The main flow path exhaust port or the branch flow path exhaust port and the common path exhaust port may be closed by a sealing member.

In the analytical tool according to the present invention, the main flow path may include a reagent cell positioned upstream from the detection cell in the sample flow direction and including a reagent layer, and the branch flow path may branch from between the detection cell and the reagent cell. In this case, the detection cell includes an additional reagent layer containing a coloring reagent, and the reagent layer contains an electron mediator for mediating electron transfer between the coloring reagent and the sample.

DESCRIPTION OF THE REFERENCE SIGNS 1, 1' microdevice (analytical tool)
21, 21' flow path
22 common path
24, 24' branch flow path
25 first reagent cell (reagent cell)
26 second reagent cell (detection cell)
27 first reagent layer (reagent layer)
28 second reagent layer (additional reagent layer)
29, 29' water stop portion
31 main flow path exhaust port
32 common path exhaust port
33 sealing member (for main flow path exhaust port)
34 sealing member (for common path exhaust port)
35' branch flow path exhaust port
36' sealing member (for branch flow path exhaust port)

BEST MODE FOR CARRYING OUT THE INVENTION

The present invention will be described below with reference to first and second embodiments shown in the accompanying drawings.

First, a microdevice according to the first embodiment of the present invention will be described with reference to FIGS. 1-4.

Figure 1:
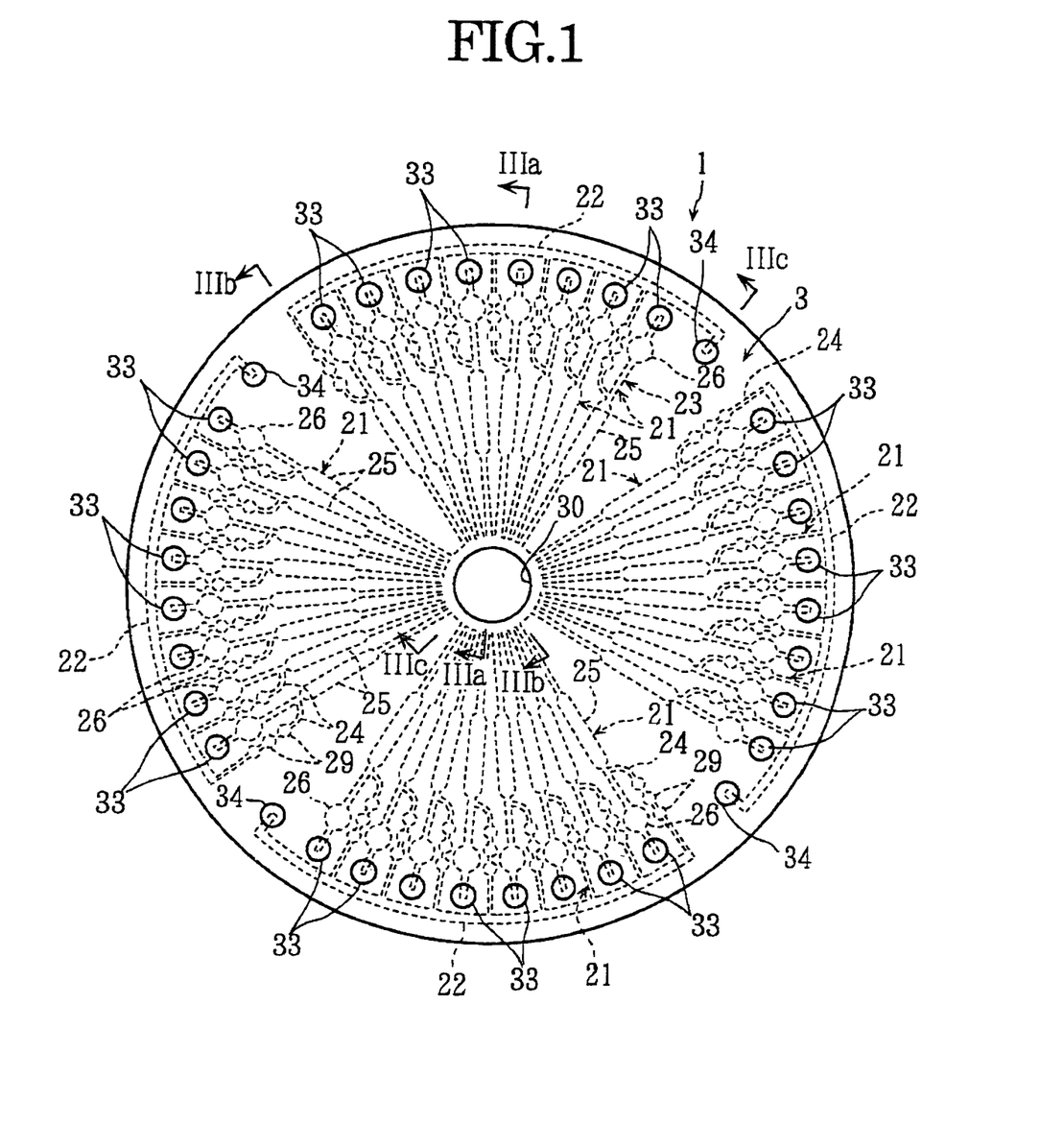
FIG. 1 is a plan view showing a microdevice according to a first embodiment of the present invention.
Figure 2:
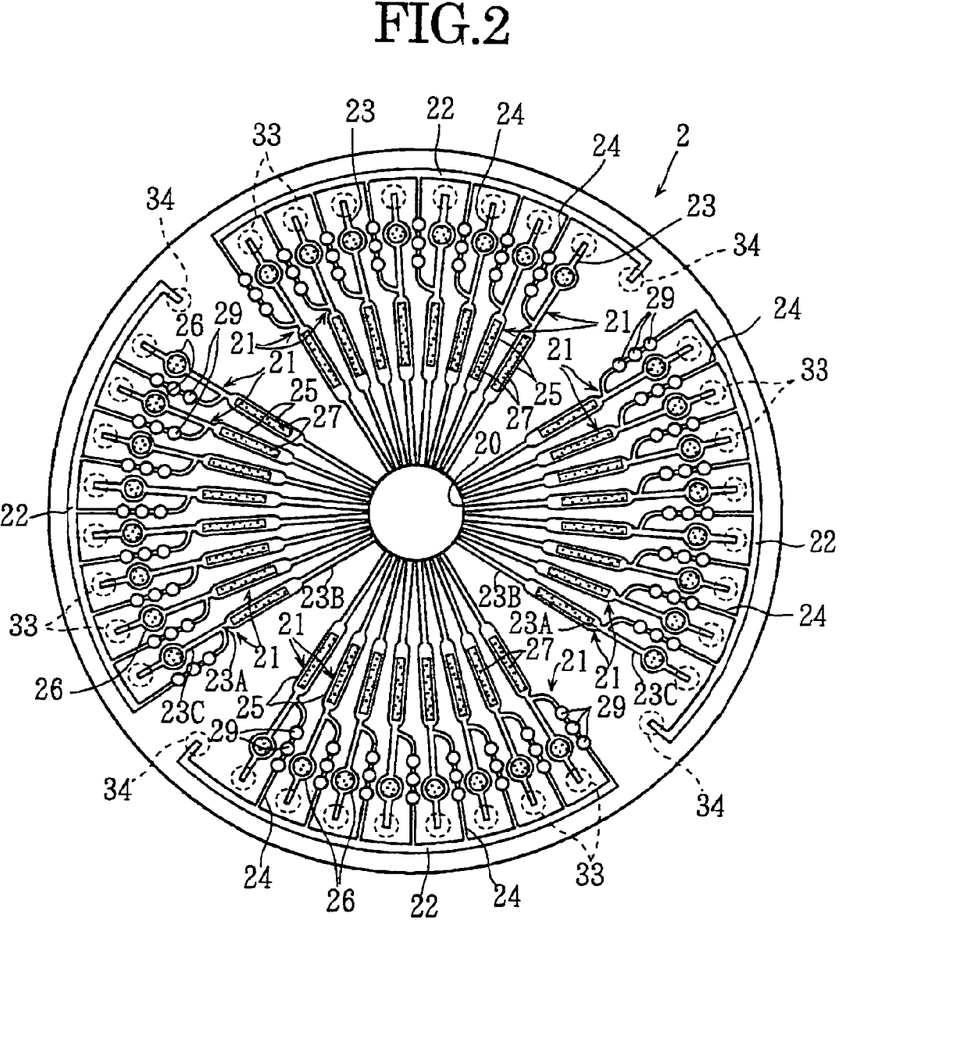
FIG. 2 is a plan view of a substrate of the microdevice shown in FIG. 1.
Figures 3A, 3B:
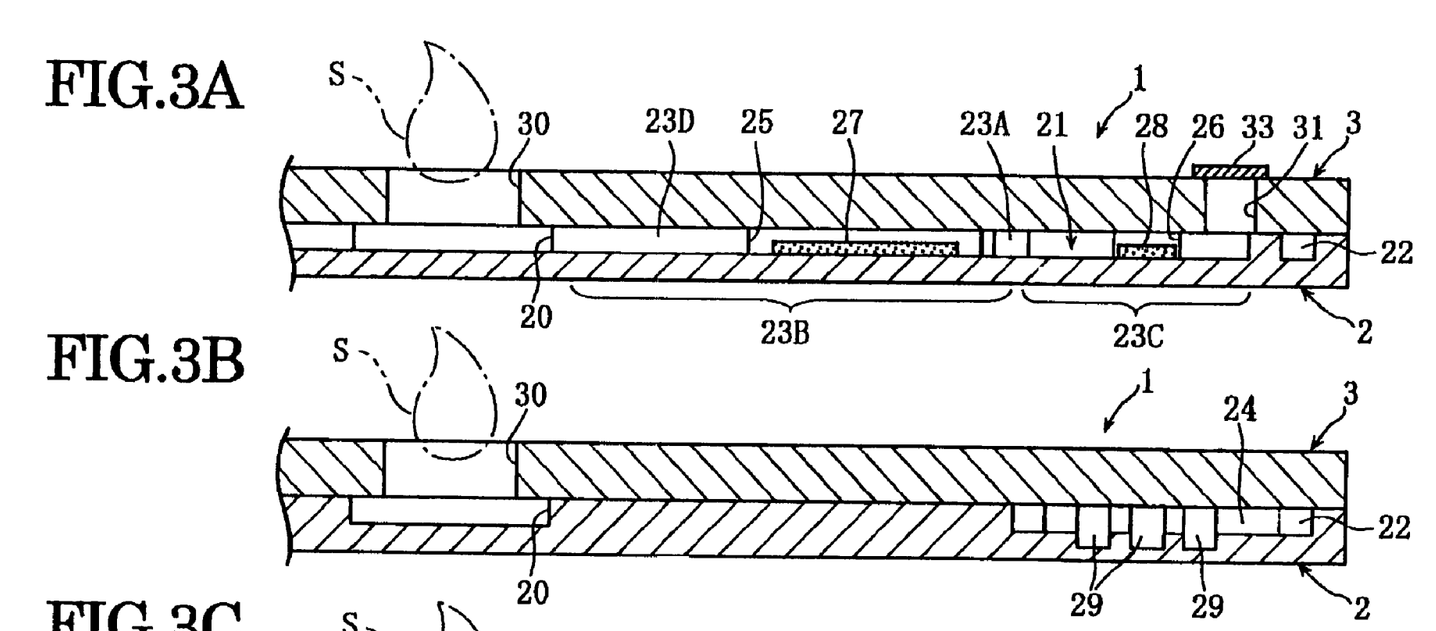
FIG. 3A is a sectional view taken along lines IIIa-IIIa in FIG. 1.
FIG. 3B is a sectional view taken along lines IIIb-IIIb in FIG. 1
Figure 3C:
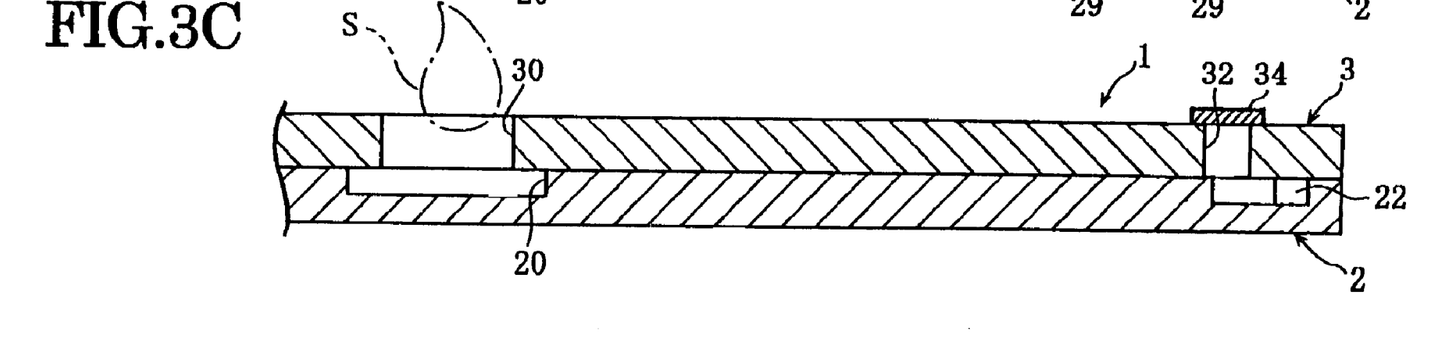
FIG. 3C is a sectional view taken along lines IIIc-IIIc in FIG. 1.

The microdevice 1 shown in FIGS. 1-3 is used for analyzing a sample by an optical technique. In use, the microdevice is mounted to an analyzer (not shown). The microdevice 1 is configured as a disposable type, including a substrate 2 and a cover 3.

The substrate 2 is in the form of a circular plate as a whole and formed with a liquid receiving portion 20, a plurality of flow paths 21 and four common paths 22.

The liquid receiving portion 20, used for retaining a sample to be introduced into each of the flow paths 21, comprises a columnar recess formed at the center of the substrate 2.

The flow paths 21 are radially arranged as a whole and divided into four groups correspondingly to the number of the common paths 21. Each of the flow paths 21 is used for moving the sample by capillarity and includes a main flow path 23 and a branch flow path 24.

As better shown in FIG. 3A, the main flow path 23 includes an upstream portion 23B extending between the liquid receiving portion 20 and a branch portion 23A, and a downstream portion 23C extending from the branch portion 23A to a position directly before the common path 22.

The upstream portion 23B includes a first reagent cell 25. A first reagent layer 27 is provided in the first reagent cell 25. The first reagent layer 27 is in a solid state which is to dissolve upon contact with a sample and contains an electron mediator and an oxidoreductase, for example.

The downstream portion 23C includes a second reagent cell 26. A second reagent layer 28 is provided in the second reagent cell 26. The second reagent layer 28 is in a solid state which is to dissolve upon contact with a sample and contains a color former which develops a color upon reaction with a particular component contained in the sample.

The electron mediator, oxidoreductase and color former to be used can be appropriately selected from conventionally known ones in accordance with the kind of the particular component to be analyzed. The reagent to be contained in the first and the second reagent layers 27, 28 is not limited to those described above and may be varied in various ways.

The branch flow path 24 is provided for causing the sample to be supplied to the first reagent cell 25 but not supplied to the second reagent cell. The branch flow path 24 branches from the main flow path 21 at the branch portion 23A located between the first reagent cell 25 and the second reagent cell 26. The branch flow path 24 is connected to the common path, so that capillary force will act in the branch flow path by discharging gas from the common path 22 to the outside. The branch flow path 24 is provided with three water stop portions 29.

Each of the water stop portions 29 is configured to stop the movement of the sample in the branch flow path 24. The water stop portion 29 comprises a generally columnar recess, where the cross sectional area of the recess in a direction perpendicular to the flow direction is larger than the cross sectional area of other portions of the branch flow path 24. Specifically, the height and width of the cross section of the water stop portion 29 in the perpendicular direction mentioned above are larger than those of other portions of the branch flow path 24. Thus, the branch flow path 24 includes portions which are stepped and increased in width. Due to the provision of the water stop portions 29, the movement of the sample through the branch flow path 24 is suppressed at the stepped portion.

As the means to provide a water stop portion 29, in addition to or instead of forming a stepped portion (i.e., changing the cross sectional area), a water-absorbent material may be provided in the branch flow path 24, or part of the inner surface of the branch flow path 24 may be subjected to water-repellent treatment. That is, the water stop portion 29 may have any structure as long as it allows the movement of gas before the sample reaches the water stop portion and stops the movement of the sample when the sample reaches the water stop portion. The number of the water stop portions 29 may not be three as long as the aim can be achieved.

Examples of water-absorbent material which can be employed for the water stop portion 29 include porous water-absorbent material and water-swellable or water-curable polymeric material. Examples of porous water-absorbent material include a foamed body (sponge), knitted fabric, woven fabric, nonwoven fabric and paper. Examples of water-swellable or water-curable polymeric material include CMC, CMC—Na, polyethylene oxide and bridged materials of these as well as water-absorbent polymer, water-soluble protein such as gelatin, water-swellable acryl and water-curable acryl.

The water-repellent treatment can be performed by various known techniques. Typically, coating with a fluorine-based resin may be employed.

Each of the common paths 22, which is used for discharging gas from the branch flow paths 24, communicates with a common path exhaust port 32, which will be described later. The common path 22 has an arcuate shape extending along the circumference of the substrate 2.

The substrate 2 having the above-described structure may be formed by resin molding using an acrylic resin such as polymethyl methacrylate (PMMA) or a transparent resin such as polydimethyl siloxane. The liquid receiving portion 20, the flow paths 21 and the common path 22 can be formed at the same time in the resin molding process by contriving the shape of the mold.

As shown in FIGS. 1 and 3, the cover 3 comprises a transparent circular plate as a whole and is formed with a sample introduction port 30, a plurality of main flow path exhaust ports 31 and four common path exhaust ports 32.

The sample introduction port 30, which is used for introducing a sample, comprises a through-hole. The sample introduction port 30 is provided at the center of the cover 3 and directly above the liquid receiving portion 20 of the substrate 2.

Each of the main flow path exhaust ports 31 comprises a through-hole and is used for discharging gas from the downstream portion 23C of the main flow path 21. Each of the main flow path exhaust ports 31 is positioned directly above the downstream end of the corresponding main flow path 21 in the substrate 2. Thus, the plurality of main flow path exhaust ports 31 are located on the same circle. The upper opening of each main flow path exhaust port 31 is closed by a sealing member 33.

Each of the common path exhaust ports 32 comprises a through-hole communicating with the corresponding common path 22 and is arranged on the circle on which the main flow path exhaust ports 31 are arranged. The upper opening of each common path exhaust port 32 is closed by a sealing member 34.

Similarly to the substrate 2, the cover 3 having the above-described structure may be formed by resin molding using a transparent resin material. The sample introduction port 30, the plurality of main flow path exhaust ports 31 and the four common path exhaust port 32 can be formed at the same time in the resin molding process.

The sample analysis using the microdevice 1 is conducted in the manner described below.

Figures 4A, 4B, 4C:
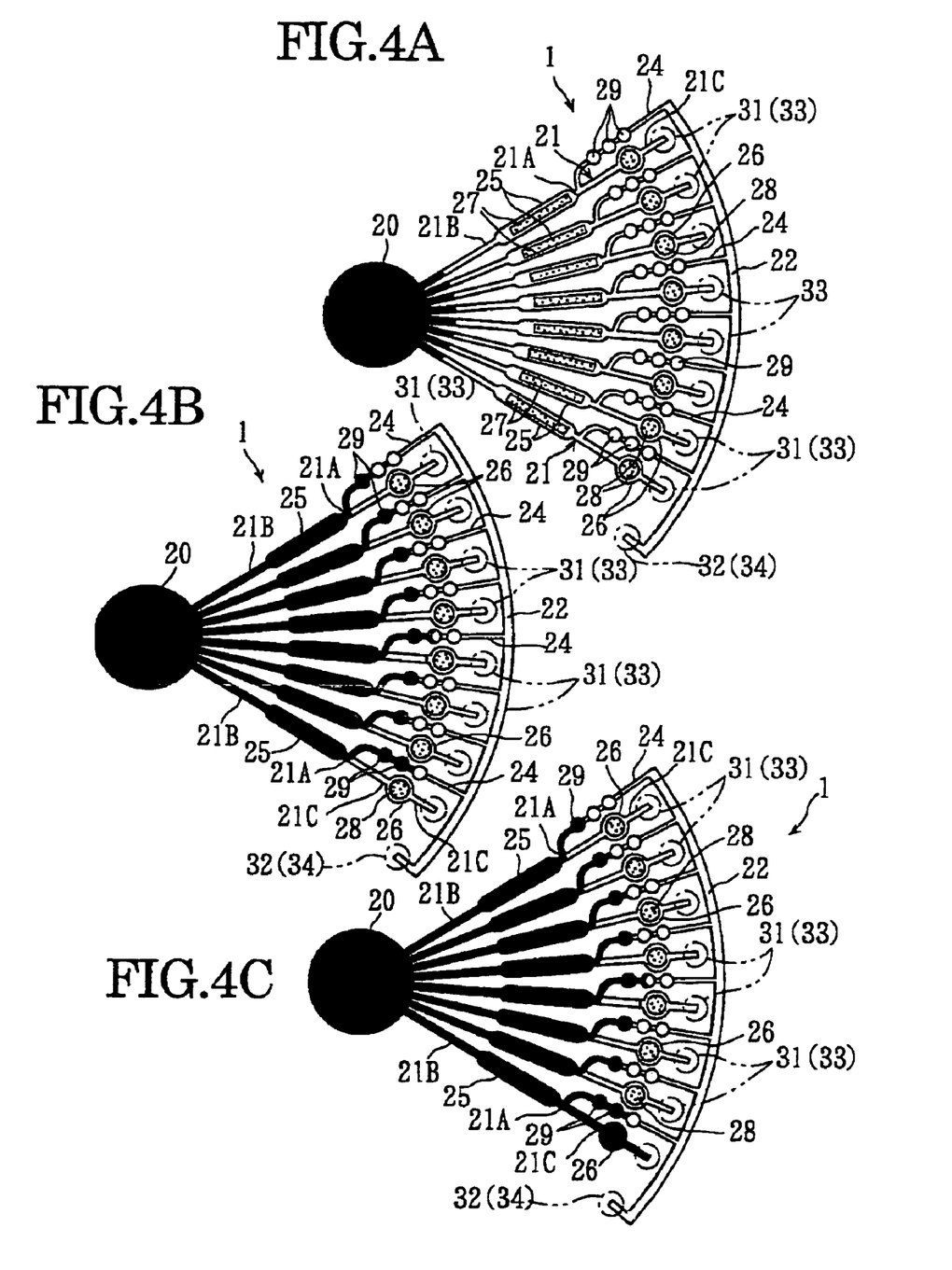
FIG. 4 is a schematic view for describing the operation of the microdevice shown in FIG. 1.

First, a sample S to be analyzed is supplied to the microdevice 1 through the sample introduction port 30. Since the main flow path exhaust ports 31 and the branch flow path exhaust ports 32 are closed by the sealing members 33 and 34, most of the sample S is retained in the liquid receiving portion 20, while part of the sample S is introduced into the main flow paths 21, as shown in FIG. 4A.

Then, the common path exhaust port 32 is opened by forming a hole in the sealing member 34. As a result, the inside of the upstream portion 23B of the main flow path 21 on the upstream side of the branch portion 23A and the inside of the branch flow path 24 communicate with the outside through the common path 22. Thus, in the flow paths 21 connected to the same common path 22, capillary force becomes effective in the upstream portions 23B and the branch flow paths 24, so that the sample S retained in the liquid receiving portion 20 is collectively introduced into the branch flow paths 24 of these flow paths 21 through the upstream portions 23B. The movement of the sample in each of the branch flow paths 24 is stopped by any of the three water stop portions 29 provided in the branch flow path 24. As a result, the movement of the sample in the main flow path 21 is stopped, and the sample introduced into the branch flow path 24 is prevented from flowing into the common path 22. In this connection, use may be made of a detector configured for determining whether the liquid has reached the water stop portion 29 based on the change in the amount of light monitored at the water stop portion 29.

As noted above, the first reagent cell 25 including the first reagent layer 27 is provided in the upstream portion 23B. Thus, when the sample is introduced into the upstream portion 23B, the first reagent layer 27 is dissolved to form a first reagent liquid. When the first reagent layer 27 contains an electron mediator and an oxidoreductase, electrons are taken from the particular component contained in the sample by the oxidoreductase and supplied to the electron mediator. That is, the first reagent liquid of the first reagent cell 25 is ready to react with the reagent contained in the second reagent layer 28 of the second reagent cell 26.

Then, the main flow path exhaust ports 31 are opened by forming holes in the sealing members 33. In the case where the amount of light at the water stop portion 29 is monitored, the holes may be formed in the sealing members 33 when a predetermined time has lapsed after the change in the amount of light is detected. In this manner, the reaction time of the reagent can be controlled. The sealing members 33 (main flow path exhaust ports 31) and the sealing member 34 (common path exhaust port 32) are arranged on the common circle. Thus, the holes in the sealing members 33 can be formed successively using the same mechanism as that used for forming a hole in the sealing member 34 while successively turning the microdevice 1 through a predetermined angle. The holes in the sealing members 33 and 34 may be formed by laser beam irradiation. In this case, the same laser diode may be used for forming the holes in the sealing members 33 and 34.

Alternatively, use may be made of a plurality of laser emitting sources for simultaneously forming the holes in the sealing members 33 connected to the same common path 22. Instead of utilizing laser irradiation, other techniques such as sticking a needle-like member into the sealing members may be employed to form holes in the sealing members 33 and 34.

When the main flow path exhaust port 31 is opened, the downstream portion 23C of the corresponding main flow path 21 communicates with the main flow path exhaust port 31. As a result, capillary force becomes effective in the upstream portion 23B of the main flow path 21. Thus, the sample (first reagent liquid) stopped in the upstream portion 23B starts to move in the downstream portion 23C. As a result, the second reagent cell 26 is filled with the sample (first reagent liquid), and the second reagent layer 28 in the second reagent cell 26 is dissolved to form a second reagent liquid. A particular component (e.g. electron mediator) in the second reagent liquid reacts with the reagent (e.g. color former) contained in the second reagent layer 28.

When a predetermined time has lapsed from the start of the reaction at the second reagent cell 26, photometry of the second reagent cell 26 is performed in a predetermined order. Based on the results of the photometry, e.g. the concentration of a particular component in the sample is computed.

As described above, in the microdevice 1, the sample introduced into the flow paths 21 is prevented from flowing unduly into the common path 22. Thus, even when the plurality of flow paths 21 of the microdevice 1 involve variations in e.g. volume (cross sectional area) due to an error in the manufacturing process, it is possible to prevent the capillary force to act in each of the flow paths 21 from reducing due to the variations. Accordingly, the movement of the sample does not stop before a sufficient amount of sample is supplied to the second reagent cell 26. Further, the speed of the movement of the sample into the second reagent cell 26 does not reduce considerably. Thus, even when the flow paths 21 of the microdevice 1 involve variations caused in the manufacturing process, the influence of the variations on the accuracy of the sample analysis is suppressed, and the reliability of the analysis accuracy is enhanced.

A microdevice according to a second embodiment of the present invention will be described below with reference to FIGS. 5 and 6. In these figures, the elements which are identical or similar to those of the microdevice according to the first embodiment are designated by the same reference signs as those used for the first embodiment, and the description thereof will be omitted.

Figure 5:
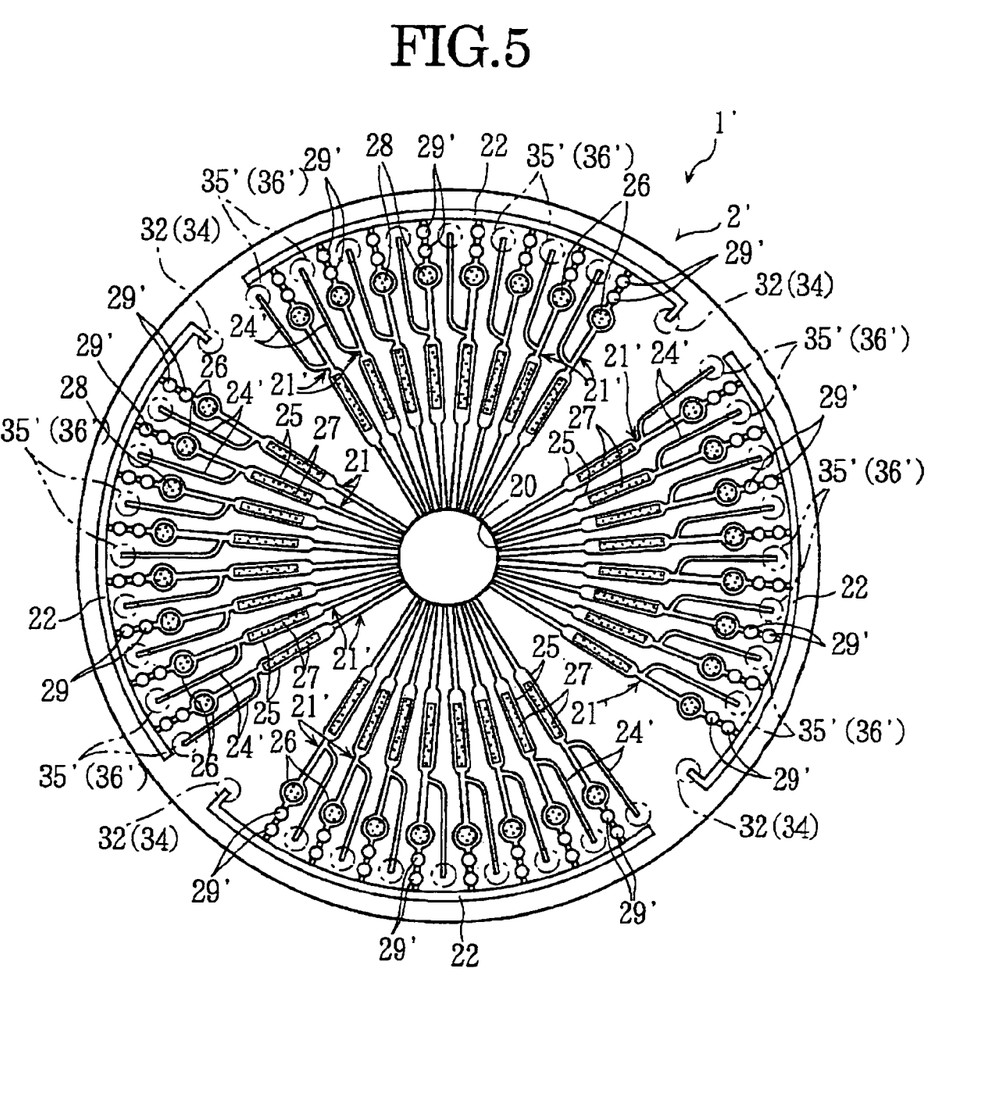
FIG. 5 is a plan view showing a substrate of a microdevice according to a second embodiment of the present invention.

Similarly to the microdevice 1 according to the first embodiment, the microdevice 1' shown in FIGS. 5 and 6 includes flow paths 21' and common paths 22. However, the microdevice 1' differs from the microdevice 1 (FIGS. 1-4) in the structure of the flow paths 21'.

Specifically, each of the flow paths 21' includes a main flow path 23' and a branch flow path 24', as in the microdevice 1 of the first embodiment (FIGS. 1-4).

Each of the main flow paths 23' communicates with the common path 22 at the downstream end thereof. The main flow path 23' is provided with two water stop portions 29' located between a second reagent cell 26 and the common path 22.

Each of the water stop portions 29' comprises a generally columnar recess, and the cross sectional area of the recess in a direction perpendicular to the flow direction is larger than that of a portion of the main flow path 23' between the second reagent cell 26 and the common path 22. Thus, portions which are stepped and increased in width exist between the second reagent cell 26 of the main flow path 23' and the common path 22. As the means to provide a water stop portion 29', in addition to or instead of forming a stepped portion (i.e., changing the cross sectional area), a water-absorbent material may be arranged in the branch flow path 24' or part of the inner surface of the branch flow path 24' may be subjected to water-repellent treatment. The number of the water stop portions 29' may not be one as long as the aim can be achieved.

Each of the branch flow paths 24' does not communicate with the common path 22 but communicates with a branch flow path exhaust port 35'. The branch flow path exhaust ports 35' and common path exhaust ports 32 are arranged on the same circle. The branch flow path exhaust ports are closed by sealing members 36'.

Figures 6A, 6B, 6C:
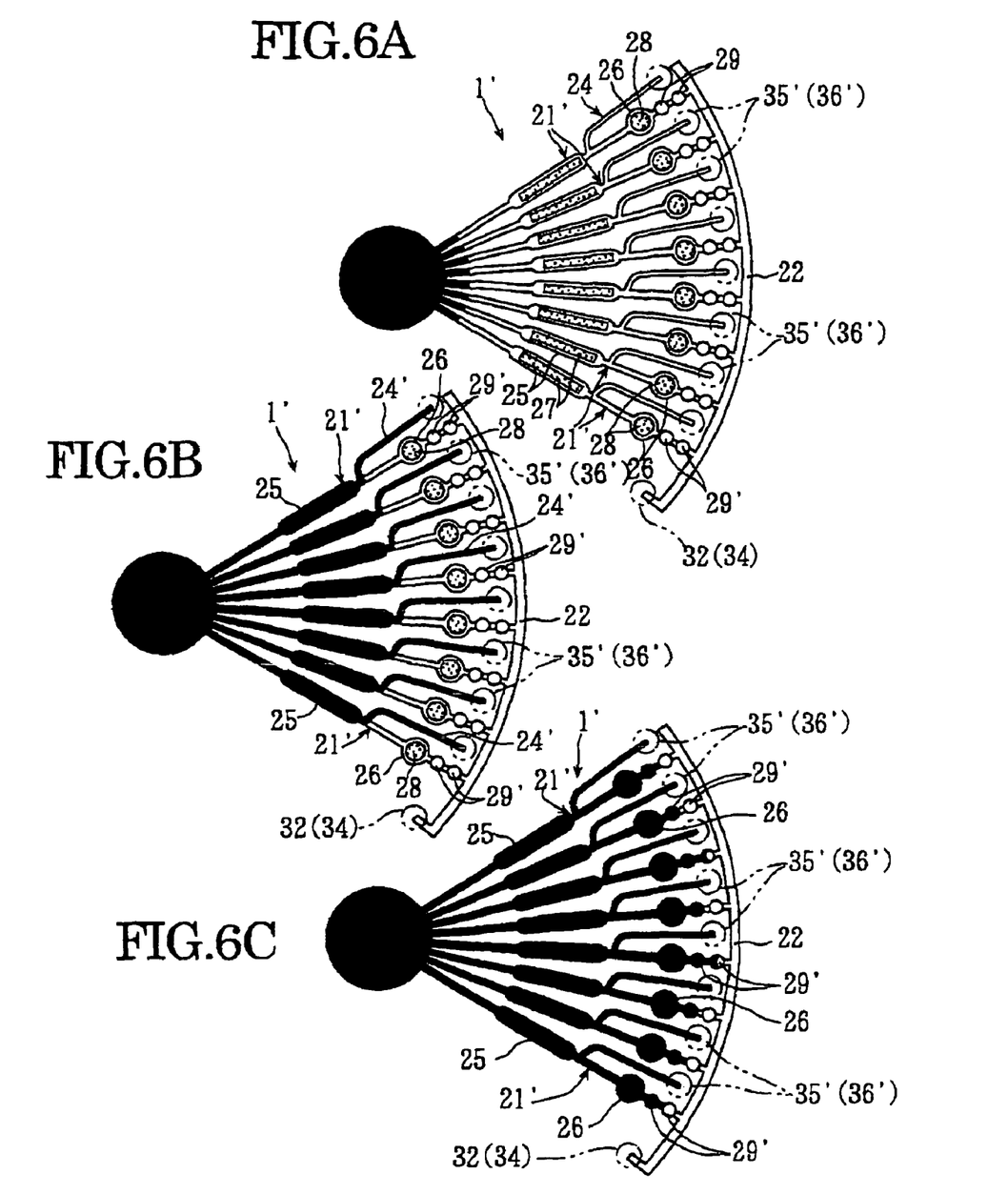
FIG. 6 is a schematic view for describing the operation of the microdevice shown in FIG. 5.

To perform sample analysis using the microdevice 1', a sample is introduced into the liquid receiving portion 20 through the sample introduction port 30, as shown in FIG. 6A. Then, a hole is formed in each of the sealing members 36'. As a result, the upstream portion 23B of the main flow path 21 and the branch flow path 24 communicate with the outside through the branch flow path exhaust port 35'. Thus, as shown in FIG. 6A, the sample is introduced into the upstream portion 23B and the branch flow path 24, and the first reagent layer 27 in the first reagent cell 25 dissolves.

Then, a hole is made in the sealing member 34 to open the common path exhaust port 32. This allows the downstream portions 23C' of the main flow paths 23' of the group connected to the common path 22 to communicate with the outside through the common path 22. Consequently, as shown in FIG. 6C, the sample moves from the branch portions 23A' of the main flow paths 23' toward the second reagent cells 26. In the flow paths 21' of the same group, the sample is introduced collectively into the second reagent cells 26. The movement of the sample stops at the water stop portion 29' provided between each of the second reagent cells 26 and the common path 22. In this way, the sample is prevented from unduly flowing into the common path 22. Thus, in the microdevice 1' again, the sample does not flow into the common path 22 and is properly introduced into the second reagent cell 26, so that the analysis accuracy is enhanced, as with the microdevice 1 (FIGS. 1-4) according to the first embodiment of the present invention.

The present invention is not limited to the first and the second embodiments but may be changed in design in various ways. For instance, the present invention is also applicable to an analytical tool which does not include the first reagent cells 25 and includes the second reagent cells 26 only. The present invention is not limited to an analytical tool designed to analyze a sample by an optical technique but is also applicable to an analytical tool designed to analyze a sample by an electrochemical technique.

The invention claimed is:

1. An analytical tool comprising a plurality of flow paths and at least one common path connecting the plurality of flow paths to each other, the plurality of flow paths each including a detection cell for detecting a particular component contained in a sample and being configured to move the sample by capillarity, wherein each of the plurality of flow paths includes a water stopper for preventing the sample from flowing into the common path.

2. The analytical tool according to claim 1, wherein the water stopper suppresses movement of the sample by having, in a direction perpendicular to a sample flow direction at a target portion, a cross sectional area differing from a cross sectional area at a portion near the target portion.

3. The analytical tool according to claim 2, wherein the water stopper includes at least one recess, and wherein a stepped portion is provided between the recess and a portion near the target portion.

4. The analytical tool according to claim 1, wherein the water stopper includes a water-absorbent material.

5. The analytical tool according to claim 4, wherein the water stopper includes at least one recess, and wherein the water-absorbent material is provided in the recess.

6. The analytical tool according to claim 4, wherein the water-absorbent material is porous water-absorbent material, water-swellable polymeric material or water-curable polymeric material.

7. The analytical tool according to claim 1, wherein the water stopper is provided by performing water-repellent treatment with respect to a target portion.

8. The analytical tool according to claim 7, wherein the water stopper includes at least one recess, and wherein the water-repellent treatment is performed with respect to an inner surface of the recess.

9. The analytical tool according to claim 1, wherein each of the flow paths includes a main flow path in which the detection cell is provided and a branch flow path branching from the main flow path on an upstream side of the detection cell in a sample flow direction.

10. The analytical tool according to claim 9, wherein the main flow path-does not communicate with the common path, whereas the branch flow path communicates with the common path, and wherein the water stopper is provided in the branch flow path.

11. The analytical tool according to claim 10, wherein the flow paths are radially arranged, wherein the main flow path includes a main flow path exhaust port for discharging gas from the detection cell, and wherein the common path includes a common path exhaust port for discharging gas from the common path, the common path exhaust port and the main flow path exhaust port being arranged on a common circle.

12. The analytical tool according to claim 11, wherein each of the main flow path exhaust port and the common path exhaust port is closed by a sealing member.

13. The analytical tool according to claim 10, wherein the main flow path includes a reagent cell positioned upstream from the detection cell in a sample flow direction and including a reagent layer, and wherein the branch flow path branches from between the detection cell and the reagent cell.

14. The analytical tool according to claim 13, wherein the detection cell includes an additional reagent layer containing a coloring reagent, and wherein the reagent layer contains an electron mediator for mediating electron transfer between the coloring reagent and the sample.

15. The analytical tool according to claim 9, wherein the main flow path communicates with the common path, whereas the branch flow path does not communicate with the common path, and wherein the water stopper is provided in the main flow path at a position downstream from the detection cell.

16. The analytical tool according to claim 15, wherein the flow paths are radially arranged, wherein the branch flow path includes a branch flow path exhaust port for discharging gas from the branch flow path, and wherein the common path includes a common path exhaust port for discharging gas from the common path, the common path exhaust port and the branch flow path exhaust port being arranged on a common circle.

17. The analytical tool according to claim 16, wherein each of the branch flow path exhaust port and the common path exhaust port is closed by a sealing member.

18. The analytical tool according to claim 15, wherein the main flow path includes a reagent cell positioned upstream from the detection cell in a sample flow direction and including a reagent layer, and wherein the branch flow path branches from between the detection cell and the reagent cell.

19. The analytical tool according to claim 18, wherein the detection cell includes an additional reagent layer containing a coloring reagent, and wherein the reagent layer contains an electron mediator for mediating electron transfer between the coloring reagent and the sample.

* * * * *